United States Patent [19]

Reilly, Jr. et al.

[11] Patent Number: 5,258,544
[45] Date of Patent: Nov. 2, 1993

[54] SYNTHESIS OF ALDEHYDES USEFUL IN THE PREPARATIONS OF HMG-COA REDUCTASE INHIBITORS

[75] Inventors: Laurence W. Reilly, Jr., Doylestown; Ching T. Tsuei; Walter Rodriquez, both of Lansdale; Thomas Goetzen, Collegeville, all of Pa.

[73] Assignee: Rhone-Poulenc Rorer Pharmaceuticals Inc., Collegeville, Pa.

[21] Appl. No.: 664,913

[22] Filed: Mar. 5, 1991

[51] Int. Cl.$^5$ .................... C07C 69/76; C07C 69/00; C07C 45/00

[52] U.S. Cl. .................... 560/107; 560/129; 560/231; 560/241; 568/424; 568/435; 568/436; 568/554; 568/589; 568/631; 568/659; 568/660; 568/661

[58] Field of Search .............. 558/388; 568/424, 436, 568/584, 631, 660; 560/8, 100, 107, 129

[56] References Cited

U.S. PATENT DOCUMENTS

| | | | |
|---|---|---|---|
| 3,901,896 | 8/1975 | Albright | 568/424 |
| 4,180,520 | 12/1979 | Verbrugge et al. | 558/388 |
| 4,224,254 | 9/1980 | Sauer et al. | 568/436 |
| 4,438,269 | 3/1984 | Guziec, Jr. | 568/424 |
| 4,463,195 | 7/1984 | Marti et al. | 568/424 |
| 4,500,721 | 2/1985 | Yamachika et al. | 568/436 |
| 4,521,630 | 6/1985 | Wattimena et al. | 568/424 |
| 4,540,811 | 9/1985 | Rizkalla | 560/100 |
| 4,855,488 | 8/1989 | Gude et al. | 560/8 |
| 4,863,957 | 9/1989 | Neuenschwander et al. | 549/292 |
| 4,900,754 | 2/1990 | Regan et al. | 514/460 |

FOREIGN PATENT DOCUMENTS

3639158 5/1988 Fed. Rep. of Germany .
0038336 2/1985 Japan .

OTHER PUBLICATIONS

Synthesis, D. Adams and S. Bhatnagar, "The Prins Reaction", 661-672 (1977).

*Primary Examiner*—C. Warren Ivy
*Assistant Examiner*—A. A. Owens
*Attorney, Agent, or Firm*—Raymond S. Parker, III; Martin F. Savitzky

[57] ABSTRACT

Disclosed is a process for the preparation of 2-aryl-1-cyclohexene-1-carboxaldehydes from 1-arylcyclohexenes which are intermediates for trans-6-[(2-arylsubstituted cycloalkenyl and substituted cycloalkyl)alkenyl and alkyl]-3,4,5,6-tetrahydro-2H-pyran-2-ones.

7 Claims, No Drawings

SYNTHESIS OF ALDEHYDES USEFUL IN THE PREPARATIONS OF HMG-COA REDUCTASE INHIBITORS

BACKGROUND OF THE INVENTION

1. Field of the Invention

This invention relates to a method for the preparation of trans-6-[(2-aryl-substituted cycloalkenyl and substituted cycloalkyl)alkenyl and alkyl]-3,4,5,6-tetrahydro-2H-pyran-2-ones. More particularly, the invention relates to a novel method for the preparation of 2-aryl-1-cyclohexene-1-carboxaldehydes from 1-arylcyclohexenes which are intermediates for trans-6-[(2-arylsubstituted cycloalkenyl and substituted cycloalkyl)alkenyl and alkyl]-3,4,5,6-tetrahydro-2H-pyran-2-ones. The latter compounds, their corresponding ring opened hydroxy acids and pharmaceutically acceptable salts thereof are potent inhibitors of the enzyme 3-hydroxy-3-methyl-glutaryl-coenzyme A reductase (hereinafter HMG-CoA reductase).

2. Reported Developments

Inhibitors of HMG-CoA are effective in lowering blood plasma cholesterol level as well as inhibiting the biosynthesis of cholesterol in humans. As such, inhibitors of HMG-CoA are useful in the prevention and treatment of coronary heart diseases. The prior art recognizes the importance of such compounds, e.g., Bethridge et al., Brit. Med. J., 4,500 (1975) and Brown et al., Scientific American, 58 Nov. (1984). Illustrative references directed to such compounds follow.

U.S. Pat. No. 4,681,893 to B. D. Roth pertains to trans-6-[2-(3-or 4-carboxamido-substituted pyrrol-1-yl)alkyl]-4-hydroxypyran-2-ones useful as hypocholesterolemic agents.

U.S. Pat. No. 4,668,669 to Hoffman et al. discloses semi-synthetic analogs of compactin and mevinolin and the dihydro and tetrahydro analogs thereof for antihypercholesterolemic application.

U.S. Pat. No. 4,282,155 to Smith et al., is directed to 6(R)-[2-(8'-Etherified-hydroxy-2', 6'-dimethylpolyhydronaphthyl-1')ethyl]-4(R)-hydroxy-3,4,5,6-tetrahydro-2H-pyran-2-ones for inhibition of biosynthesis of cholesterol.

U.S. Pat. No. 4,567,289 to Willard et al., relates to methyl, ethyl, n-propyl, 2-(acetylamino)ethyl, or 1-(2,3-dihydroxy)propyl ester of E-(3R,5S)-7-(4'-fluoro-3,3',5trimethyl-[1,1'-biphenyl]-2-yl)-3,5-dihydroxy-6heptenoic acid that are HMC-CoA reductase inhibitors.

U.S. Pat. No. 4,611,067 to Volante et al., discloses a process for the preparation of HMG-CoA reductase inhibitors which contain a 4-hydroxy-3,4,5,6-tetrahydro-2H-pyran-2-one moiety.

U.S. Pat. No. 4,900,754 to Regan et al., discloses trans-6-[(2-aryl-substituted cycloalkenyl and substituted cycloalkyl)alkenyl and alkyl]-3,4,5,6-tethydro-2H-pyran-2-ones and methods for their preparation. While the preparative methods are satisfactory to obtain the desired compounds, they are somewhat cumbersome and long. The present invention is directed to a much shorter, more economical method which is especially suited to large-scale manufacturing.

SUMMARY OF THE INVENTION

In one aspect the present invention concerns a process for the preparation of a cycloalkene ester of formula I

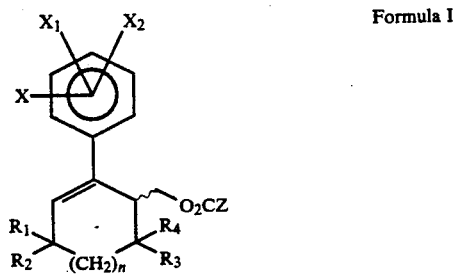

Formula I comprising: reacting a cycloalkene of formula II

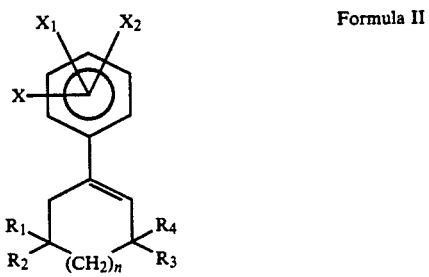

Formula II with formaldehyde in the presence of an organic acid wherein:

X, $X_1$ and $X_2$ are independently: F, Cl, Br, OH, $CF_3$, R, alkoxy, aryl, $NO_2$, NH(CO)R, $N(R)_2$, or $S(O)_m R$;

$R_1$ and $R_2$ are independently: H, alkyl, aryl, OR, F, Cl, or Br;

$R_3$ and $R_4$ are independently: H or lower alkyl;

R is H or lower alkyl;

n is 0–2;

m is 0–2; and

Z is H, alkyl or aryl.

In another aspect the present invention concerns a process for the preparation of an allylic aldehyde of formula III

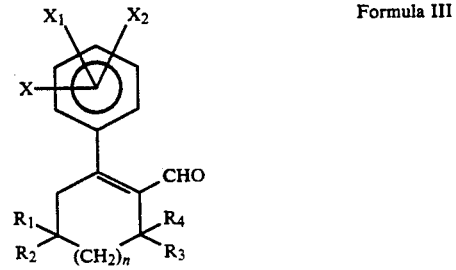

Formula III comprising: hydrolyzing a cycloalkene ester of formula I

Formula I

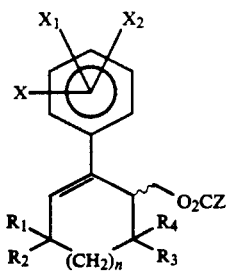

to a homoallylic alcohol of formula IV

Formula IV

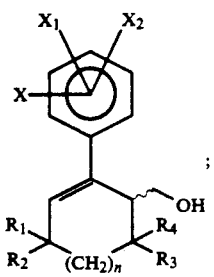

oxidizing said homoallylic alcohol to a homoallylic aldehyde of formula V

Formula V

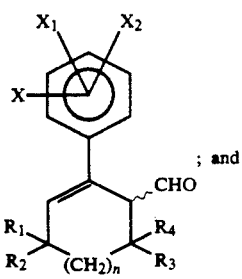

epimerizing said homoallylic aldehyde to said allylic aldehyde of formula III, wherein the radicals X, $X_1$, $X_2$, R, $R_1$, $R_2$, $R_3$ and Z denote the radicals previously defined.

In another aspect of the invention a process for the preparation of trans-6-[(2-aryl-substituted cycloalkenyl and substituted cycloalkyl)alkenyl and alkyl]3,4,5,6-tetrahydro-2H-pyran-2-ones, the corresponding ring-opened hydroxyacids derived therefrom and pharmaceutically acceptable salts thereof is provided which are potent inhibitors of HMG-CoA reductase.

Specifically, the invention provides for the preparation of compounds prepared of formula VI Formula VI

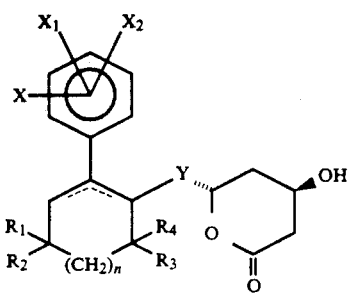

its hydroxy acids, and pharmaceutically acceptable salts thereof wherein

Y is —CHR—, —CHRCHR—, —CHRCHRCHR—, or —RC=CR—;

X, $X_1$ and $X_2$ are independently: F, Cl, Br, OH, $CF_3$, R, alkoxy, aryl, $NO_2$, NH(CO)R, $N(R)_2$, or $S(O)_mR$;

$R_1$ and $R_2$ are independently: H, alkyl, aryl, OR, F, Cl, or Br;

$R_3$ and $R_4$ are independently: H or lower alkyl;

R is H or lower alkyl;

n is 0–2;

m is 0–2; and the dotted lines between carbons 1 and 2 or 2 and 3 in the cycloalkyl ring represent an optional double bond, comprising the steps of:

(a) reacting an alicyclic ketone with an aryl organometallic reagent to produce a tertiary aryl carbinol;

(b) converting said tertiary aryl carbinol to a cycloalkene by addition of an acid;

(c) converting said cycloalkene to an ester by reaction with formaldehyde in the presence of an organic acid;

(d) hydrolyzing said ester with an aqueous base to a homoallylic alcohol;

(e) oxidizing said homoallylic alcohol to a homoallylic aldehyde with an oxidizing agent;

(f) epimerizing said homoallylic aldehyde to a conjugated aldehyde;

(g) reacting said conjugated aldehyde with an activated acetonitrile derivative in the presence of a base to obtain a nitrile;

(h) reducing said nitrile to aldehyde;

(i) reacting said aldehyde with acetoacetic acid ester in the presence of a base to obtain a hydroxyketoester;

(j) reducing said hydroxyketoester to obtain a syn-dihydroxyester;

(k) hydrolyzing said syn-dihydroxyester to obtain a syndihydroxyacid; and (l) cyclizing said syn-dihydroxyacid to obtain said lactone of formula VI.

DETAILED DESCRIPTION OF THE INVENTION

As employed above and throughout the specification, the following terms, unless otherwise indicated, shall be understood to have the following meaning:

"Lower alkyl" means a saturated or unsaturated aliphatic hydrocarbon which may be either straight- or branched-chained containing from 1 to 4 carbon atoms.

"Alkyl" means a saturated or unsaturated aliphatic hydrocarbon which may be either straight- or branched-chained containing from one to ten carbon atoms.

"Alkoxy" means an alkyl oxy group in which "alkyl" is as previously defined. Lower alkoxy groups are preferred which include methoxy, ethoxy, n-propoxy, i-propoxy, and n-butoxy.

"Aryl" means an aromatic hydrocarbon radical having 6 to 10 carbon atoms. The preferred aryl groups are phenyl, substituted phenyl and naphthyl. The term "substituted" means "alkyl", "halogen" or "hydroxyalkyl" substitution.

The pharmaceutically acceptable salts of the present invention include those formed from sodium, potassium, calcium, aluminum, lithium, magnesium, zinc, lysine, arginine, procaine, ethylenediamine and piperazine.

The invention encompasses optical and stereoisomers of the compounds and mixtures thereof defined by the structural formula.
The general procedure for producing the compounds of the present invention is as follows wherein:
Y, X, $X_1$, $X_2$, $R_1$, $R_2$, $R_3$, $R_4$, Z n and m are as previously defined and $R_5$ is alkyl or aralkyl.
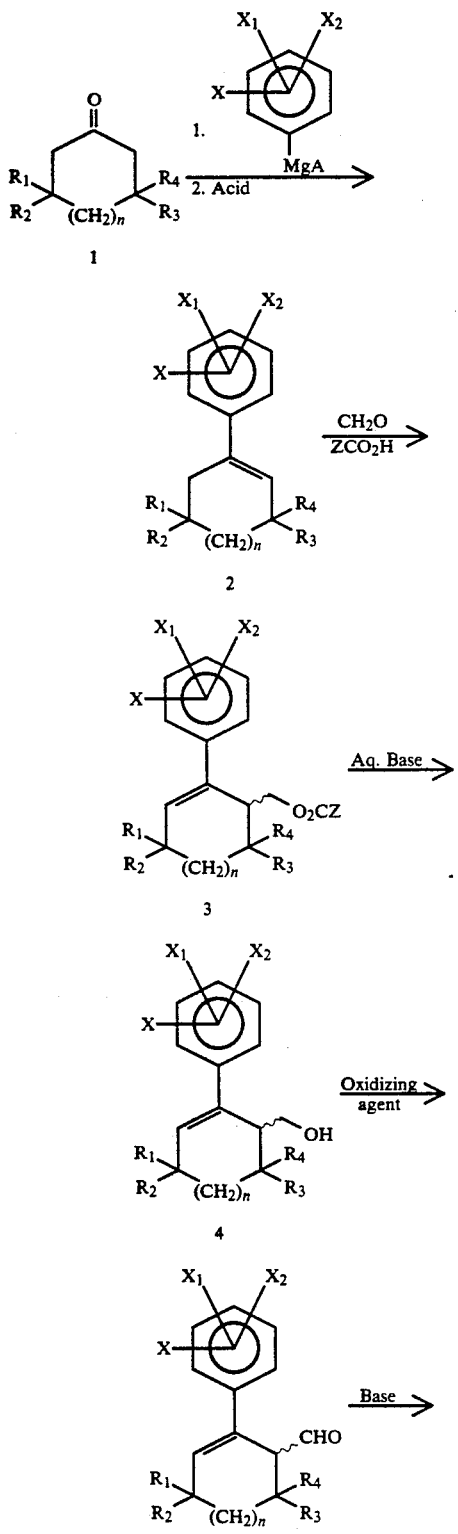
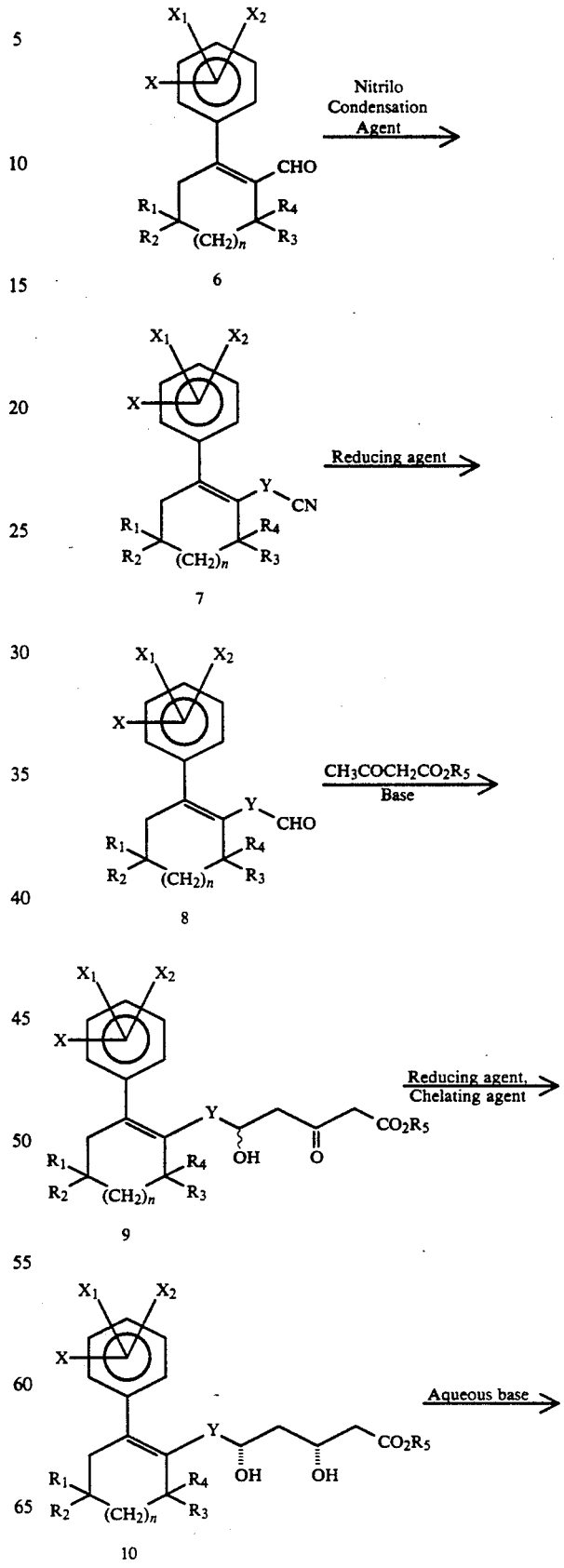

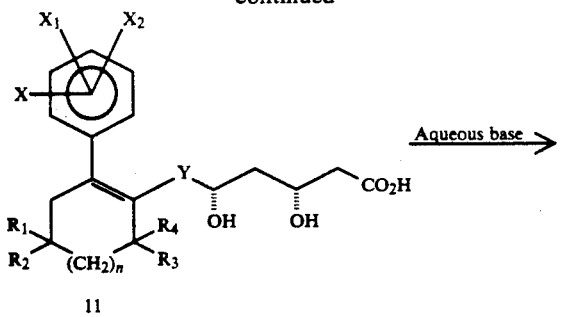

11

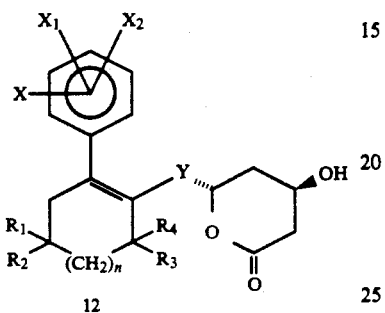

12

Reference is now made to the general scheme of making the compounds of the present invention.

An alicyclic ketone of the type denoted by #1 is reacted with an aryl organometallic reagent, i.e., an aryl Grignard reagent, to give an intermediate tertiary aryl carbinol. The tertiary aryl carbinol is converted, without isolation, to a cycloalkene of the type denoted by #2 by the addition of an acid to the reaction mixture. The acid used may be either an organic acid, such as formic and acetic acid, or an inorganic acid, such as sulfuric and hydrochloric acid. The cycloalkene is then converted to an ester, denoted by #3, by reaction with a form of formaldehyde, such as formalin, paraformaldehyde, 1,3,5-trioxane and the like, in the presence of an organic acid such as formic or acetic acid. Preferably, the reaction should be conducted in the presence of a catalytic quantity of an inorganic acid, such as sulfuric acid. Product #3 is then hydrolyzed with an aqueous base, such as sodium or potassium hydroxide to a homoallylic alcohol, denoted by #4. Product #4 is oxidized to a homoallylic aldehyde denoted by #5 in the presence of an oxidizing agent of the transition metal variety, such as pyridinium chlorochromate, or other suitable oxidizing agents, such as pyridine-sulfur trioxide complex in DMSO in the presence of a teritary amine or dicyclohexylcarbodiimide in DMSO in the presence of a organic acid catalyst. Product #5 is then epimerized with a non-condensing, non-nucleophilic base, such as sodium hydroxide, to produce the conjugated aldehyde #6. Reaction of the conjugated aldehyde with an activated acetonitrile derivative, such as dialkyl cyanomethylphosphonate or a phosphonium salt of said nitrile, cyanoacetic acid or its esters, or acetonitrile and a base, such as LDA or t-BuOK, leads to the nitrile #7. The so-obtained product then is reduced with a suitable reducing agent that is capable of reducing a nitrile, such as diisobutylaluminum hydride to give the aldehyde #8. The aldehyde is then reacted with acetoacetic acid ester, such as $CH_3COCH_2CO_2R_5$ wherein $R_5$ is alkyl or aralkyl, in the presence of a base, such as LDA, to produce the hydroxyketoester #9. Product #9 is then reduced stereoselectively to produce the syn-dihydroxyester #10. Reduction may be accomplished with a reducing agent including sodium borohydride and trialkylborane; sodium borohydride and dialkylalkoxyborane; or sodium cyanoborohydride and chlorotitanium triisopropoxide. Product #10 is hydrolyzed under basic conditions similar to that used in the hydrolysis of product #3, to give the syn-dihydroxyacid #11. Product #11 is cyclized with alkyl chloroformate, such as $ClCO_2R_5$ wherein $R_5$ is alkyl or aralkyl, and a base; or by activating as an appropriate ester or amide; or by heating in a suitable solvent, such as toluene at reflux, to obtain the lactone #12.

The starting materials and reagents may be obtained from chemical supply houses, such as Aldrich Chem. Co. but may also be synthesized in accordance with methods known in the art.

The following preparative methods will further illustrate the invention.

EXAMPLE I

A) 1-(4-Fluoro-3-methylphenyl)-6-hydroxymethyl-3,3,5,5-tetramethylcyclohexene formate ester To a stirred slurry of 85.3 g (0.346 mol) of 1-fluoro-2-methyl-4-(3,3,5,5)-tetramethyl-1-cyclohexen-1-yl)benzene in 470 ml of 90% formic acid is added 78 ml (1.04 mol) of 37% $CH_2O$ solution. The reaction mixture is refluxed for 6 hr. The slurry is then allowed to cool to 60°–65° C. and 470 ml of saturated NaCl solution is added. The reaction mixture is extracted twice with 200 ml of hexanes and the extracts are dried over anhydrous $Na_2SO_4$. After filtration, the solution is concentrated in vacuo at 40° C. to yield 100.5 g (95%) of golden oil, which can be used directly in the next step. A pure sample of 1-(4-fluoro-3-methylphenyl)-6-hydroxymethyl-3,3,5,5-tetramethylcyclohexene formate ester can be obtained via column chromatography on silica gel.

Anal. calcd. for: $C_{19}H_{25}FO_2$: C, 74.97; H, 8.28. Found: C, 75.14; H, 8.38.

B) 1-(4-Fluoro-3-methylphenyl)-6-hydroxymethyl-3,3,5,5-tetramethylcyclohexene

To a solution of 100.5 g (0.330 mol) of crude 1-(4-fluoro-3-methylphenyl)-6-hydroxymethyl-3,3,5,5-tetramethylcyclohexene formate ester in 400 ml of methanol is added 36 ml (0.689 mol) of 50% NaOH solution. The reaction mixture is stirred for 30 min. Ice water (400 ml) is then added and the reaction mixture is extracted twice with 200 ml of hexanes. The extracts are dried over anhydrous $Na_2SO_4$, filtered and concentrated in vacuo at 40° C. to yield 97.6 g of amber oil. This oil is percolated through 1 kg of silica gel (70–230 mesh) and eluted with hexanes until non-polar impurities are removed. Elution is the switched to EtOAc:hexanes::1:24 (v/v) and continued until recovery is complete. Concentration in vacuo at 40° C. gives 61.4 g (67%) of 1-(4-fluoro-3-methylphenyl)-6-hydroxymethyl-3,3,5,5-tetramethylcyclohexene: m.p. 40°–42° C.;

Anal. calcd. for: $C_{18}H_{25}FO$: C, 78.22; H, 9.22. Found: C, 77.20; H, 8.95.

C) 2-(4-Fluoro-3-methylphenyl)-4,4,6,6-tetramethylcyclohex-2-enecarboxaldehyde.

Into a slurry of 61.4 g (0.222 mol) of 1-(4-fluoro-3-methylphenyl)-6-hydroxymethyl-3,3,5,5-tetramethylcyclohexene in 330 ml of DMSO and 194 ml of triethylamine is poured a solution of 106.0 g (0.666 mol) of sulfur trioxide pyridine complex in 330 ml of DMSO. The reaction mixture is then stirred for 30 min. Ice (660 g) is added and the reaction mixture is extracted twice with 300 ml of hexanes. The extracts are then backwashed thrice with 280 ml of 10% HCl, dried over anhydrous Na$_2$SO$_4$, filtered and concentrated in vacuo at 40° C. to yield 57.1 g (94%) of 2-(4-fluoro-3-methylphenyl)-4,4,6,6-tetramethylcyclohex-2-enecarboxaldehyde suitable for use in the next step. A pure sample of 2-(4-fluoro-3-methylphenyl)-4,4,6,6-tetramethylcyclohex-2-enecarboxaldehyde can be obtained via column chromatography on silica gel.

Anal. calcd. for: C$_{18}$H$_{23}$FO: C, 78.80; H, 8.45. Found: C, 77.84; H, 8.51.

D) 2-(4-Fluoro-3-methylphenyl)-4,4,6,6-tetramethylcyclohex-1-enecarboxaldehyde.

To a solution of 57.1 g (0.208 mol) of 2-(4-fluoro-3-methylphenyl)-4,4,6,6-tetramethylcyclohex-2-enecarboxaldehyde in 370 ml of methanol is added 16.8 g (0.311 mol) of anhydrous NaOMe. The reaction mixture is stirred for 30 min. Water (370 ml) is then added and the reaction mixture is extracted twice with 200 ml of hexanes. The extracts are dried over anhydrous Na$_2$SO$_4$, filtered and concentrated in vacuo at 40° C. to yield 53.0 g of crude 2-(4-fluoro-3-methylphenyl)-4,4,6,6-tetramethylcyclohex-2-enecarboxaldehyde. This is dissolved in 20 ml of hexanes and stored at −20° C. overnight. Pure 2-(4-fluoro-3-methylphenyl)-4,4,6,6-tetramethylcyclohex-1-enecarboxaldehyde is then collected, washed twice with 20 ml of cold hexanes and dried in vacuo to constant weight to yield 31.5 g (55%) of the pure compound: m.p. 50.5°–51.5° C.

Anal. calcd. for: C$_{18}$H$_{23}$FO: C, 78.80; H, 8.45; F, 6.92. Found: C, 78.98; H, 8.26; F, 6.76.

EXAMPLE 2

2-(4-Fluoro-3-methylphenyl)-4,4,6,6-tetramethylcyclohex-1-enecarboxaldehyde

To a mixture of 20 kg of 1-fluoro-2-methyl-4-(3,3,5,5-tetramethyl-1-cyclohexen-1-yl)benzene, 72 kg of 96% formic acid and 3.6 kg of 1,3,5-trioxane, 96 g of 70% benzoyl peroxide catalyst was added and the bath was heated to reflux for about 3 hours. The mixture was then cooled to room temperature and 48 kg of heptane was added with stirring. The phases were allowed to separate and the bottom layer was discarded. The top layer was washed with water, then 48 kg of methanol and 7.2 kg of 50% aqueous sodium hydroxide were added. The mixture was stirred for about 10 minutes, washed with water and dried with 10 kg of anhydrous sodium sulfate. The sodium sulfate was filtered off and the filter cake was washed with 10 kg of heptane. To the combined filtrates, 96 kg of dimethyl sulfoxide and 28 kg of triethylamine were added. Sulfur trioxide/pyridine complex (36 kg) was then charged portionwise at 30°–35° C. The batch was agitated for 15 minutes and the reaction was quenched with 96 kg of iced water. The phases were allowed to separate and the bottom layer was discarded. The top layer was washed with dilute hydrochloric acid and with brine. Methanol (48 kg) and 50% sodium hydroxide (4.8 kg) were added and the batch was stirred at 21°–25° C. for one hour. Ice (0.6 kg) was added and the mixture was stirred for 15 minutes. The phases were allowed to separate and the bottom layer was discarded. The top solution was washed with brine and concentrated in vacuo to remove the volatiles. The residue was dissolved in 22 kg of isopropanol and 2.8 kg of water. The mixture was then cooled to about −10° C., seeded and stirred for 16 hours. The crystallized product was filtered off, washed with cold aqueous isopropanol and dried to constant weight.

Yield: 8.5 kg of 2-(4-fluoro-3-methylphenyl)-4,4,6,6-tetramethylcyclohex-1-enecarboxaldehyde; m.p. 50.5°–51.5° C.

EXAMPLE 3

2-(4-Fluoro-3-methylphenyl)-4,4,6,6-tetramethylcyclohex-1-enecarboxaldehyde

To a mixture of 200 g of glacial acetic-acid, 200 g of 1-fluoro-2-methyl-4-(3,3,5,5-tetramethyl-1-cyclohexen-1-yl)benzene and 35.4 g of 1,3,5-trioxane, a catalytic quantity (4.0 g) of concentrated sulfuric acid was added and the batch was heated to 106°–110° C. for 1¼ hours. The mixture was then cooled to 30° C. and partitioned between 100 ml of water and 200 ml of heptane. The bottom layer was discarded and to the remaining solution 100 ml of methanol was added. A solution of 96 g of 85% potassium hydroxide in 100 ml of water was then added and the reaction mixture was heated to 68°–72° C. for 1¼ hours. The batch was then cooled to 30° C. and the phases were allowed to separate. The bottom layer was discarded and the top layer was concentrated in vacuo until 25% of the total volume was distilled off. The remaining solution was diluted with 100 ml of heptane and 182 g of triethylamine. To the resulting mixture, a solution of 324 g of sulfur trioxide/pyridine complex in 535 g of dimethyl sulfoxide and 78.3 g of triethylamine was added at 30°–35° C. The batch was stirred at 30°–35° C. for ½ hour, then cooled to about 20° C. and quenched with 600 g of iced water. The phases were allowed to separate and the bottom layer was discarded. The top layer was diluted with 100 ml of methanol and 50% sodium hydroxide solution (90 g) was added. The reaction mixture was stirred for 1¼ hours at 30°–34° C. Water (100 ml) was added and the phases were allowed to separate at room temperature. The bottom layer was discarded and the top solution was concentrated in vacuo to remove the solvent. The residue was dissolved in 200 ml of ethanol, the solution was cooled to about 3° C., seeded and the product was allowed to crystallize overnight. The solids were filtered off, washed with 80 ml of cold ethanol and dried to constant weight. Yield: 100 g of 2-(4-fluoro-3-methylphenyl)-4,4,6,6-tetramethylcyclohex-1-enecarboxaldehyde; m.p. 50.5°–51.5° C.

The compounds of formula VI are useful as hypocholesterolemic or hypolipidemic agents by virtue of their ability to inhibit the biosynthesis of cholesterol through inhibition of the enzyme HMG-CoA reductase. Having such ability, the compounds are incorporated into pharmaceutically acceptable carriers and administered to a patient in need of such cholesterol biosynthesis inhibition orally or parenterally. Such pharmaceutical formulations to contain at least one compound according to the invention.

Suitable carriers include diluents or fillers, sterile aqueous media and various non-toxic organic solvents. The compositions may be formulated in the form of tablets, capsules, lozenges, trochees, hard candies, powders, acqueous suspensions, or solutions, injectable solutions, elixirs, syrups and the like and may contain one or more agents selected from the group including sweetening agents, flavoring agents, coloring agents and preserving agents, in order to provide a pharmaceutically acceptable preparation.

The particular carrier and the ratio of active compound to carrier are determined by the solubility and chemical properties of the compounds, the particular mode of administration and standard pharmaceutical practice. For example, excipients such as lactose, sodium citrate, calcium carbonate and dicalcium phosphate and various disintegrants such as starch, alginic acid and certain complex cilicates, together with lubricating agents such as magnesium sterate, sodium lauryl sulphate and talc, can be used in producing tablets. For a capsule form, lactose and high molecular weight polyethylene glycols are among the preferred pharmaceutically acceptable carriers.

Where aqueous suspensions for oral use are formulated, the carrier can be emulsifying or suspending agents. Diluents such as ethanol, propylene glycol, and glycerin and their combinations can be employed as well as other materials.

For parenteral administration, solutions or suspensions of these compounds in aqueous alcoholic media or in sesame or peanut oil or aqueous solutions of the soluble pharmaceutically acceptable salves can be employed.

The dosage regimen in carrying out the methods of this invention is that which insures maximum therapeutic response until improvement is obtained and thereafter the minimum effective level which gives relief. Doses may vary, depending on the age, severity, body weight and other conditions of the patients but are ordinarily in the area of 5 mg/kg to 500 mg/kg of body weight in oral administration; such may, of course be given in two to four divided doses. With other forms of administration equivalent or adjusted doses will be administered depending on the route of administration.

The utility of the claimed compounds is measured by the test methods described hereunder. The methods are based on the articles: "Purification of 3-hydroxy-3-methylgutaryl coenzyme A reductase from rat liver" by Kleinsek et al., Proc. Nat'l. Acad. Sci. USA, Vol. No. 4, pp 1431-1435, April 1977 Biochemistry; "Mevinolin: A highly potent competitive inhibitor of hydroxy methyl glutaryl-coenzyme A reductase and a cholesterol-lowering agent" by Alberts et al., Proc. Nat'l. Acad. Sci. USA, Vol 77, pp 3951-3961, July 1980, Biochemistry; "Effects of ML-236B on cholesterol metabolism in mice rats: Lack of hypocholesterolemic activity in normal animals" by Ends et al., Biochimica et Biophysica Acta, 575 (1979) 266-276; and "Evidence of regulation of 3-hydroxy-3-methylglutaryl-coenzyme A reductase activity and cholesterol synthesis in nonhepatic tissues of rat") by Balasubramaniam et al., Proc. Nat'l. Sci. USA, Vol. 73, No. 8, pp. 2564-2568, Aug. 1986, Biochemistry.

The first method used (designated HMGR Screen) was as follows. Male rats were acclimated to an alternate 12 hour light-dark cycle for a period of 2-3 weeks. The animals, weighing 180-230 g, were fed ad libitum a rat chow containing 2% cholestyramine for 5 days prior to sacrifice at the mid-dark period. Liver microsomes were prepared and HMGR enzyme was solubilized from the microsomes by freeze-thaw manipulation in high ionic strength buffer. The enzyme preparation was stored at $-80°$ C. in 300 $\mu$l portion samples. Prior to use, the enzyme was activated at 37° C. for 30 minutes in a reaction mixture. The reaction mixture contained in a volume of 240 $\mu$l:0.14M potassium phosphate buffer (pH 7.0); 0.18M KCl; 3.5 mM EDTA; 10 mM dithiothreitol; 0.1 mg/l BSA; 30,000 cpm of [$^{14}$C]HMG-CoA; 50 $\mu$M HMG-CoA, and 200 $\mu$g of solubilized enzyme with and without inhibitors (in 10 $\mu$l DMSO). After 5 minutes incubation at 37° C. the reaction was initiated with 0.2 mM NADPH. The final assay volume was 300 ml. The reaction then was terminated with 100 ml of 1N HCl. After an additional incubation for 15 minutes at 37° C. to allow for complete lactonization of the product, mevalonate, the mixture was diluted with 3 ml GDW. The diluted mixture was then poured over a 0.7×1.4 cm column containing 100-200 mesh Bio-Rex ion-exchange resin (chloride form of Bio-Rad) which was equilibrated with distilled water. With this resin the unreacted [$^{14}$C]HMG-CoA was adsorbed and the product [$^{14}$C]mevalonolactone was eluted (80% recovery) directly into scintillation vials. After the addition of 10 ml of Aquasol®, radioactivities of the samples were measured in a scintillation counter. Mevinolin (a lactone form) was then converted to its sodium salt, mevinolinic acid, by saponification in 0.1N NaOH for 60-120 minutes.

The second method (designated Ex-Vivo Non-Fasted and Ex-Vivo Fasted) used was as follows. Rats of 170-210 g were maintained on a low cholesterol diet for one week prior to use. Drugs were given orally in 0.5% methocel to both fed and fasted (fasted for 16 hours) rats. After one hour (fasted rats) and two hours (fed rats) and the rats were decapitated and their livers removed and transferred to chilled oxygenated Kreb's-Ringer-bicarbonate buffer (pH 7.4). The livers were then chopped into 0.5 mm slices using a McIlwain tissue chopper, and were suspended in the same buffer. Alquots of the suspension containing 100 mg tissue were pipetted to culture tubes which contained [$^{14}$C]sodium acetate (2 $\mu$Ci, 1 mM). The tubes were gassed with 95%$O_2$/5%$CO_2$, capped and incubated at 37° C. in a shaking water bath at 150 oscillation/min. for two hours. The final assay volume was 1.0 ml. After incubation the reaction was stopped by the addition of 1.0 ml of 15% KOH in ethanol, and the internal standard $^3$H-cholesterol was added. The tubes were recapped and the samples were saponified at 75° C. for two hours with periodic mixing. Subsequently an aliquot was removed for protein analysis using Bio-Rad's standard kit, and the remainder of the saponified samples was extracted with 10 ml of petroleum ether for 30 minutes. The lower aqueous phase was frozen in a dry-ice/alcohol mixture and the ether layer was poured into labelled tubes. The ether was then evaporated to dryness and the cholesterol was separated by thin layer chromatography on plastic silica gel plates. After visualization with iodine the cholesterol spots were cut and counted with liquid scintillation fluid.

What is claimed is:

1. A process for the preparation of a cycloalkene ester of formula I

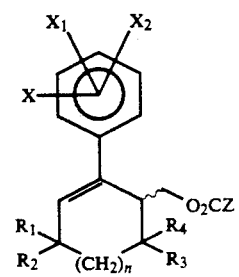

Formula I comprising: reacting a cycloalkene of the formula

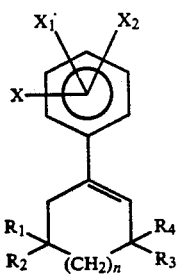

with a source of formaldehyde in the presence of an organic acid selected from the group consisting of formic or acetic acid wherein:

X, $X_1$ and $X_2$ are independently F, Cl, Br, OH, $CF_3$, R, alkoxy having 1 to 10 carbon atoms, aryl having 6 to 10 carbon atoms, $NO_2$, NH(CO)R, $N(R)_2$, or $S(O)_mR$;

$R_1$ and $R_2$ are independently H, alkyl having 1 to 10 carbon atoms, aryl having 6 to 10 carbon atoms, OR, F, Cl, or Br;

$R_3$ and $R_4$ are independently H or lower alkyl;

R is H or lower alkyl;

n is 0–2;

m is 0–2; and

Z is alkyl having 1 to 10 carbon atoms or aryl having 6 to 10 carbon atoms.

2. A compound of the formula:

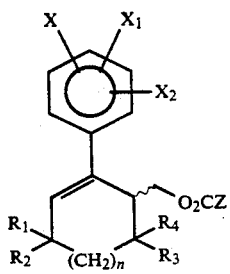

wherein:

X, $X_1$ and $X_2$ are independently halogen, OH, $CF_3$, R, alkoxy having 1 to 10 carbon atoms, aryl having 6 to 10 carbon atoms, $NO_2$, NH(CO)R, $N(R)_2$, or $S(O)_mR$;

$R_1$ and $R_2$ are independently H, alkyl having 1 to 10 carbon atoms, aryl having 6 to 10 carbon atoms, OR, or halogen;

$R_3$ and $R_4$ are independently H or lower alkyl;

R is H or lower alkyl;

n is 0–2;

m is 0–2; and

Z is alkyl having 1 to 10 carbon atoms or aryl having 6 to 10 carbon atoms.

3. A compound of the formula:

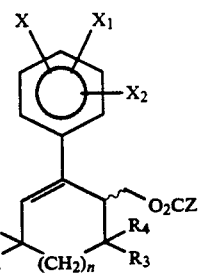

wherein:

X, $X_1$ and $X_2$ are independently halogen, OH, $CF_3$, R, lower alkoxy having 1 to 10 carbon atoms, aryl, having 6 to 10 carbon atoms $NO_2$, NH(CO)R, $N(R)_2$, or $S(O)_mR$;

$R_1$ and $R_2$ are independently H, alkyl having 1 to 10 carbon atoms, aryl having 6 to 10 carbon atoms, OR, halogen;

$R_3$ and $R_4$ are independently H or lower alkyl;

R is H or lower alkyl;

n is 0–2;

m is 0–2; and

Z is alkyl having 1 to 10 carbon atoms or aryl having 6 to 10 carbon atoms.

4. A process for the preparation of an allylic aldehyde of formula III

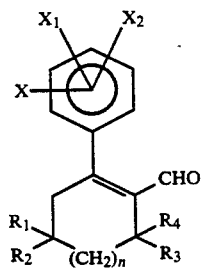

Formula III comprising: hydrolyzing the cycloalkene ester of formula I prepared according to the process of claim 1

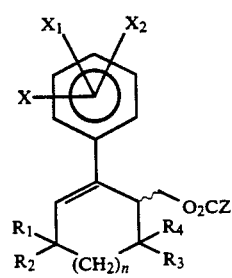

Formula I to form a homoallylic alcohol of formula IV

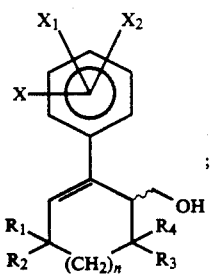

Formula IV oxidizing said homoallylic alcohol to a homoallylic aldehyde of formula V

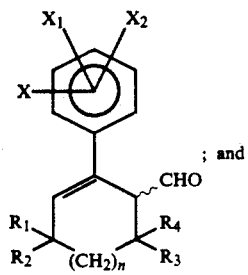

Formula V epimerizing said homoallylic aldehyde.

5. A process for the preparation of a compound of formula 8

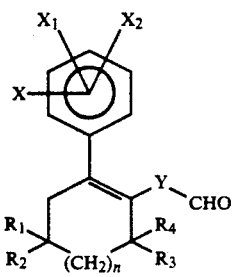

Formula 8 comprising:
reacting the allylic aldehyde prepared according to the process of claim 4 with an activated acetonitrile derivative in the presence of a base to obtain a nitrile; and
reducing said nitrile; wherein
Y is —CHR—, —CHRCHR—, —CHRCHRCHR—, or —RC═CR—.

6. A process for the preparation of a homoallylic aldehyde of formula V

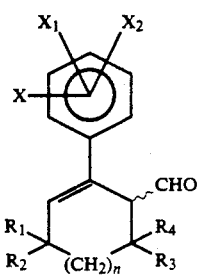

Formula V comprising: hydrolyzing a cycloalkene ester of formula I

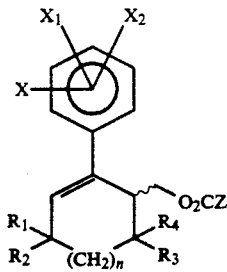

Formula I to a homoallylic alcohol of formula IV

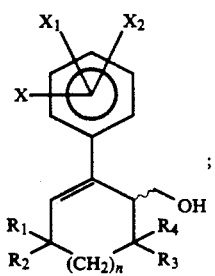

Formula IV and oxidizing said homoallylic alcohol to said homoallylic aldehyde of formula V wherein X, $X_1$ and $X_2$ are independently halogen, OH, $CF_3$, R alkoxy having 1 to 10 carbon atoms, aryl having 6 to 10 carbon atoms, $NO_2$, NH(CO)R, $N(R)_2$, or $S(O)_mR$;

$R_1$ and $R_2$ are independently H, alkyl having 1 to 10 carbon atoms, aryl having 6 to 10 carbon atoms, OR, or halogen;

$R_3$ and $R_4$ are independently H or lower alkyl;

R is H or lower alkyl;

Z is alkyl having 1 to 10 carbon atoms or aryl having 6 to 10 carbon atoms;

n is 0–2; and m is 0–2.

7. A compound of the formula:

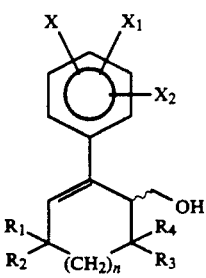

wherein:
X, $X_1$ and $X_2$ are independently halogen, OH, $CF_3$, R, alkoxy having 1 to 10 carbon atoms, aryl having 6 to 10 carbon atoms, $NO_2$, NH(CO)R, $N(R)_2$, or $S(O)_mR$;

$R_1$ and $R_2$ are independently H, alkyl having 1 to 10 carbon atoms, aryl having 6 to 10 carbon atoms, OR, or halogen;

$R_3$ and $R_4$ are independently H or lower alkyl;

R is H or lower alkyl;

n is 0–2; and m is 0–2.

* * * * *